United States Patent
Smith, III et al.

(10) Patent No.: US 9,504,638 B2
(45) Date of Patent: Nov. 29, 2016

(54) PERSONAL CLEANSING COMPOSITIONS COMPRISING ZINC PYRITHIONE

(71) Applicant: The Procter & Gamble Company, Cincinnati, OH (US)

(72) Inventors: Edward Dewey Smith, III, Mason, OH (US); Jason Edward Cook, Cincinnati, OH (US); Chunpeng Jiang, Beijing (CN); Ian David Henry, Cincinnati, OH (US); Juan Wang, Beijing (CN); Casey Patrick Kelly, Wyoming, OH (US); Xiujun Xu, Beijing (CN); Zhe Liu, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 528 days.

(21) Appl. No.: 13/890,369

(22) Filed: May 9, 2013

(65) Prior Publication Data
US 2013/0303503 A1    Nov. 14, 2013

(51) Int. Cl.
| | |
|---|---|
| *A61K 8/58* | (2006.01) |
| *A61K 8/36* | (2006.01) |
| *A61K 8/365* | (2006.01) |
| *A61Q 19/10* | (2006.01) |
| *A61K 8/27* | (2006.01) |
| *A61K 8/49* | (2006.01) |
| *C11D 9/32* | (2006.01) |

(52) U.S. Cl.
CPC . *A61K 8/58* (2013.01); *A61K 8/27* (2013.01); *A61K 8/36* (2013.01); *A61K 8/361* (2013.01); *A61K 8/365* (2013.01); *A61K 8/4933* (2013.01); *A61Q 19/10* (2013.01); *C11D 9/32* (2013.01); *A61K 2800/58* (2013.01)

(58) Field of Classification Search
None
See application file for complete search history.

(56) References Cited

U.S. PATENT DOCUMENTS

| | | | |
|---|---|---|---|
| 2,809,971 | A | 10/1957 | Bernstein et al. |
| 3,235,455 | A | 2/1966 | Judge |
| 3,281,366 | A | 10/1966 | Judge et al. |
| 3,412,033 | A | 11/1968 | Karsten |
| 3,725,547 | A | 4/1973 | Kooistra |
| 4,161,526 | A | 7/1979 | Gorman |
| 4,205,062 | A | 5/1980 | Daahn |
| 4,345,080 | A | 8/1982 | Bolich, Jr. |
| 4,379,753 | A | 4/1983 | Bolich, Jr. |

(Continued)

FOREIGN PATENT DOCUMENTS

| | | |
|---|---|---|
| EP | 0034385 B1 | 8/1981 |
| EP | 0093541 A2 | 11/1983 |

(Continued)

OTHER PUBLICATIONS

U.S. Appl. No. 14/208,821, filed Mar. 14, 2014, Smith III et al.

(Continued)

*Primary Examiner* — Necholus Ogden, Jr.

(57) ABSTRACT

The present invention relates to a personal cleansing composition with an antimicrobial effect. The personal cleansing composition is in the form of a bar soap and contains zinc pyrithione and a soap surfactant. When dispersed in an aqueous solution at 1 wt %, the personal cleansing composition of the present invention is characterized by a pH value ranging that is higher than about 9.6 and lower than about 10.3. The present invention also relates to a process for forming an antimicrobial bar soap as described hereinabove.

16 Claims, 3 Drawing Sheets

(56) References Cited

U.S. PATENT DOCUMENTS

| | | | |
|---|---|---|---|
| 4,482,715 A | 11/1984 | Trotz | |
| 4,533,736 A | 8/1985 | Trotz | |
| 4,565,693 A | 1/1986 | Marschner | |
| 4,708,863 A | 11/1987 | Bews et al. | |
| 4,714,563 A | 12/1987 | Kajs | |
| 4,818,436 A | 4/1989 | French | |
| 4,935,061 A | 6/1990 | French | |
| 4,957,658 A | 9/1990 | French | |
| 5,037,818 A | 8/1991 | Sime | |
| 5,104,645 A | 4/1992 | Cardin | |
| 5,198,140 A | 3/1993 | Joshi | |
| 5,540,860 A | 7/1996 | Hosseini et al. | |
| 5,562,995 A | 10/1996 | Kappock | |
| 5,573,699 A | 11/1996 | Jones | |
| 5,612,301 A | 3/1997 | Inman | |
| 5,714,447 A | 2/1998 | Jones | |
| 5,883,154 A | 3/1999 | Kappock | |
| 5,886,031 A | 3/1999 | Shin et al. | |
| 5,972,920 A | 10/1999 | Seidel | |
| 6,015,547 A | 1/2000 | Yam | |
| 6,017,562 A | 1/2000 | Kaufman et al. | |
| 6,017,936 A | 1/2000 | Polson et al. | |
| 6,096,122 A | 8/2000 | Kappock | |
| 6,096,297 A | 8/2000 | Jones et al. | |
| 6,162,446 A | 12/2000 | Hani et al. | |
| 6,242,007 B1 | 6/2001 | Mohseni | |
| 6,277,360 B1 | 8/2001 | Carew et al. | |
| 6,432,432 B1 | 8/2002 | Mohseni et al. | |
| 6,451,300 B1 | 9/2002 | Dunlop et al. | |
| 6,465,015 B1 | 10/2002 | Mohseni et al. | |
| 6,649,155 B1 | 11/2003 | Dunlop et al. | |
| 6,673,756 B2 | 1/2004 | Sonnenberg et al. | |
| 6,682,724 B2 | 1/2004 | Mohseni et al. | |
| 6,887,859 B2 | 5/2005 | Clapp et al. | |
| 6,974,569 B2 | 12/2005 | Dunlop et al. | |
| 7,026,308 B1 | 4/2006 | Gavin et al. | |
| 7,381,415 B2 | 6/2008 | Yokoyama et al. | |
| 7,544,367 B2 | 6/2009 | Mohseni et al. | |
| 7,674,785 B2 | 3/2010 | Gavin et al. | |
| 8,119,168 B2 | 2/2012 | Johnson et al. | |
| 8,491,877 B2 | 7/2013 | Schwartz et al. | |
| 9,333,157 B2 | 5/2016 | Jiang et al. | |
| 2002/0001605 A1 | 1/2002 | Carew | |
| 2004/0058855 A1 | 3/2004 | Schwartz | |
| 2004/0161435 A1 | 8/2004 | Gupta | |
| 2004/0186030 A1 | 9/2004 | Hofrichter | |
| 2004/0191331 A1 | 9/2004 | Schwartz et al. | |
| 2004/0213751 A1 | 10/2004 | Schwartz et al. | |
| 2005/0118276 A1 | 6/2005 | Lei et al. | |
| 2005/0244352 A1 | 11/2005 | Lemoine et al. | |
| 2006/0111259 A1 | 5/2006 | Chakrabarty et al. | |
| 2007/0009463 A1 | 1/2007 | Niebauer et al. | |
| 2007/0128147 A1 | 6/2007 | Schwartz et al. | |
| 2007/0190177 A1 | 8/2007 | Kling et al. | |
| 2008/0063618 A1 | 3/2008 | Johnson et al. | |
| 2008/0138442 A1 | 6/2008 | Johnson et al. | |
| 2008/0160093 A1 | 7/2008 | Schwartz et al. | |
| 2008/0206355 A1 | 8/2008 | Schwartz et al. | |
| 2008/0249136 A1 | 10/2008 | Annis et al. | |
| 2011/0039469 A1 | 2/2011 | Cabell et al. | |
| 2011/0197906 A1 | 8/2011 | Schwartz | |
| 2011/0197907 A1 | 8/2011 | Schwarz | |
| 2011/0200649 A1 | 8/2011 | Schwartz | |
| 2011/0200650 A1 | 8/2011 | Schwartz | |
| 2011/0201588 A1 | 8/2011 | Schwartz | |
| 2012/0039966 A1 | 2/2012 | Capretta et al. | |
| 2012/0103151 A1 | 5/2012 | Jones et al. | |
| 2012/0216408 A1 | 8/2012 | Cook et al. | |
| 2012/0219610 A1* | 8/2012 | Smith et al. | 424/409 |
| 2012/0220516 A1 | 8/2012 | Smith et al. | |
| 2012/0246851 A1 | 10/2012 | Smith, III et al. | |
| 2012/0324736 A1 | 12/2012 | Eagleton | |
| 2013/0042482 A1 | 2/2013 | Bradford et al. | |
| 2013/0045248 A1 | 2/2013 | Coffindaffer et al. | |
| 2013/0045255 A1 | 2/2013 | Smith, III et al. | |
| 2013/0045256 A1 | 2/2013 | Schwartz | |
| 2013/0045257 A1 | 2/2013 | Alwattari et al. | |
| 2013/0045263 A1 | 2/2013 | Smith, III et al. | |
| 2013/0045284 A1 | 2/2013 | Stella | |
| 2013/0045907 A1 | 2/2013 | Lanzalaco et al. | |
| 2013/0045961 A1 | 2/2013 | Smith, III et al. | |
| 2013/0048005 A1 | 2/2013 | Smith, III et al. | |
| 2013/0205959 A1 | 8/2013 | Jones et al. | |
| 2013/0222057 A1 | 8/2013 | Henshaw | |
| 2013/0280200 A1 | 10/2013 | Schwartz | |

FOREIGN PATENT DOCUMENTS

| | | |
|---|---|---|
| EP | 0158481 A2 | 10/1985 |
| EP | 0196824 A2 | 10/1986 |
| EP | 0217635 A2 | 4/1987 |
| EP | 0285388 A2 | 10/1988 |
| EP | 0468564 A2 | 1/1992 |
| JP | 2001-278863 A | 10/2001 |
| JP | 2006-176675 | 12/2004 |
| WO | 94/14408 A1 | 7/1994 |
| WO | 94/14409 A1 | 7/1994 |
| WO | 96/23850 A1 | 8/1996 |
| WO | 99/66886 A1 | 12/1999 |
| WO | 00/35413 A1 | 6/2000 |
| WO | 02/00178 A1 | 1/2002 |
| WO | 2006/110386 A1 | 10/2006 |
| WO | 2011/147941 A1 | 12/2011 |
| WO | 2012/116466 A1 | 9/2012 |

OTHER PUBLICATIONS

U.S. Appl. No. 13/856,457, filed May 22, 2013, Cook et al.
U.S. Appl. No. 14/255,714, filed Apr. 17, 2014, Jiang et al.
"The stability of 2-pyridinethiol-1-oxide, sodium salt, as a function of pH", Robert J. Fenn et al, J. Soc. Cosmet. Chem., 33, 243-248 (Aug. 1982).
"Effect of Premicellar Aggregation on the pKa of Fatty Acid Soap Solutions", J.R. Kanicky et al., Langmuir 2003, 19, 2034-2038, 2003 American Chemical Society, Published on Web Feb. 7, 2003.
"Chromatographic Behavior of Pyrithiones", Caren Anja Doose et al., Journal of Chromatography A, 1052 (2004) 103-110.
PCT International Search Report and Written Opinion for PCT/US2012/026880, dated May 29, 2012.
"Effect of Degree, Type, and Position of Unsaturation on the pKa of Long-Chain Fatty Acids", James R. Kanicky et al, Journal of Colloid and Interface Science 256, 201-207 (2002).
PCT International Search Report and Written Opinion for PCT/CN2014/072729, dated May 28, 2014.
International Search Report and Written Opinion of the International Searching Authority mailed Feb. 28, 2013, PCT/CN2012/075387, 12 pages.
Supplementary International Search Report mailed Mar. 25, 2015, PCT/CN2012/075387, 8 pages.
Supplementary European Search Report mailed Feb. 12, 2016, PCT/CN2012/075387, 6 pages.

* cited by examiner

PERSONAL CLEANSING COMPOSITIONS COMPRISING ZINC PYRITHIONE

FIELD OF THE INVENTION

The present invention relates to a personal cleansing composition comprising zinc pyrithione. More specifically, the present invention relates to a bar soap that contains stabilized zinc pyrithione.

BACKGROUND OF THE INVENTION

Pyrithione (also known as 1-Hydroxy-2-pyridinethione, 2-pyridinethiol-1-oxide, 2-mercaptopyridine-N-oxide, pyridine-2-thione-N-oxide, pyridinethione-N-oxide, 2-pyridinethione, pyridinethione, or simply "PT") has been noted for its bactericidal and fungicidal activities. Pyrithione is a bidentate ligand that forms stable complexes with most transitional metals. Metallization of pyrithione often results in highly augmented biocidial activities. Metal salts of pyrithione, such as sodium pyrithione, magnesium pyrithione, barium pyrithione, bismuth pyrithione, strontium pyrithione, copper pyrithione, zinc pyrithione, cadmium pyrithione, and zirconium pyrithione, are widely used as fungicides and bactericides in a broad spectrum of commercial products, such as metalworking fluids, lubricants, paints, cosmetics and toiletries.

Zinc pyrithione (or ZPT) is especially useful as a broad-spectrum anti-microbial agent and preservative. It is active against both gram-positive and gram-negative bacteria, as well as fungi and yeasts. Therefore, zinc pyrithione has been used in various personal care compositions, such as anti-dandruff shampoos, hair conditioners, leave-on tonics, and anti-microbial foot powders.

However, zinc pyrithione has been known to be unstable when solubilized. It may undergo transformation upon exposure to oxidizing species or certain metal cations, such as $Cu^{2+}$ and $Fe^{3+}$. The anti-microbial effect of ZPT-based personal care compositions can therefore diminish substantially over time in environments susceptible to oxidation or metallization.

There is therefore a need to form personal care compositions with stabilized zinc pyrithione.

One approach for stabilizing zinc pyrithione is to disperse the zinc pyrithione particles in a liquid carrier at a relatively low pH value of from about 4 to about 9. At this low pH level, the solubility of zinc pyrithione is limited, and a majority of the zinc pyrithione remains in a particulate form and therefore is less susceptible to attack by oxidizing species or metal cations in the solution. Since most liquid personal cleansing products (e.g., shampoos, shower gels, body washes, liquid hand soaps, and the like) are formed with carriers within this low pH range, zinc pyrithione can be easily incorporated into such liquid personal cleansing products with a relatively low risk of loss.

Despite the availability of various liquid personal cleansing products on the market, bar soap remains a popular product form for skin cleansing. Most bar soaps are characterized by a pH value of about 10.0 or higher. Such a high pH value is necessary for soap compositions in order to: (1) ensure full saponification of the triglycerides used for forming soap, and (2) effectively control microorganism growth and thereby provide a satisfactory cleansing effect.

However, inventors of the present invention discovered that at such a high pH level, zinc pyrithione becomes highly susceptible to oxidation. Although several recently commercialized soap products claim to incorporate 2% of zinc pyrithione as an active ingredient for treating chronic skin conditions, such as dandruff, scaling, flaking, itchiness, and redness, inventors of the present invention found that the detected zinc pyrithione level in these products was substantially lower than what was claimed by the manufacturers. This indicates that a majority of the zinc pyrithione in these commercial products have been oxidized and thereby was no longer effective as a biocidal agent.

Therefore, there is particularly a need for providing bar soap products with an improved zinc pyrithione retention rate and sustained anti-microbial effect.

SUMMARY OF THE INVENTION

The present invention solves the above-described zinc pyrithione stability problem by providing a personal cleansing composition that contains zinc pyrithione and at least one soap surfactant, while such personal cleansing composition is in form of a bar soap and is characterized by a pH value that is higher than about 9.6 and lower than about 10.3 when dispersed in an aqueous solution at 1 wt %. Preferably, the personal cleansing composition of the present invention is characterized by a pH value ranging from about 9.80 to about 10.25, and more preferably a pH value ranging from about 10.0 to about 10.2, when dispersed in a 1 wt % aqueous solution.

The present invention further relates to a method of forming a bar soap, including the steps of combining from about 0.01% to about 5% by weight of zinc pyrithione with from about 20% to about 95% by weight of at least one soap surfactant, and shaping the mixture to form a bar soap, while such bar soap is characterized by a pH value ranging from about 9.60 to about 10.30 when dispersed in an aqueous solution at 1 wt %. Preferably, the bar soap so formed is characterized by a pH value ranging from about 9.80 to about 10.25, and more preferably a pH value ranging from about 10.0 to about 10.2, when dispersed in a 1 wt % aqueous solution.

Preferably but not necessarily, the percentage loss of zinc pyrithione is no greater than about 10%, after the above-described personal cleansing composition or bar soap is placed at 50° C. for 12 days. More preferably, the percentage loss of zinc pyrithione so detected is no greater than about 5%, and most preferably no greater than about 2%.

These and other aspects of the present invention will become more apparent upon reading the following drawings and detailed description of the invention.

DETAILED DESCRIPTION OF THE INVENTION

Figure 1:
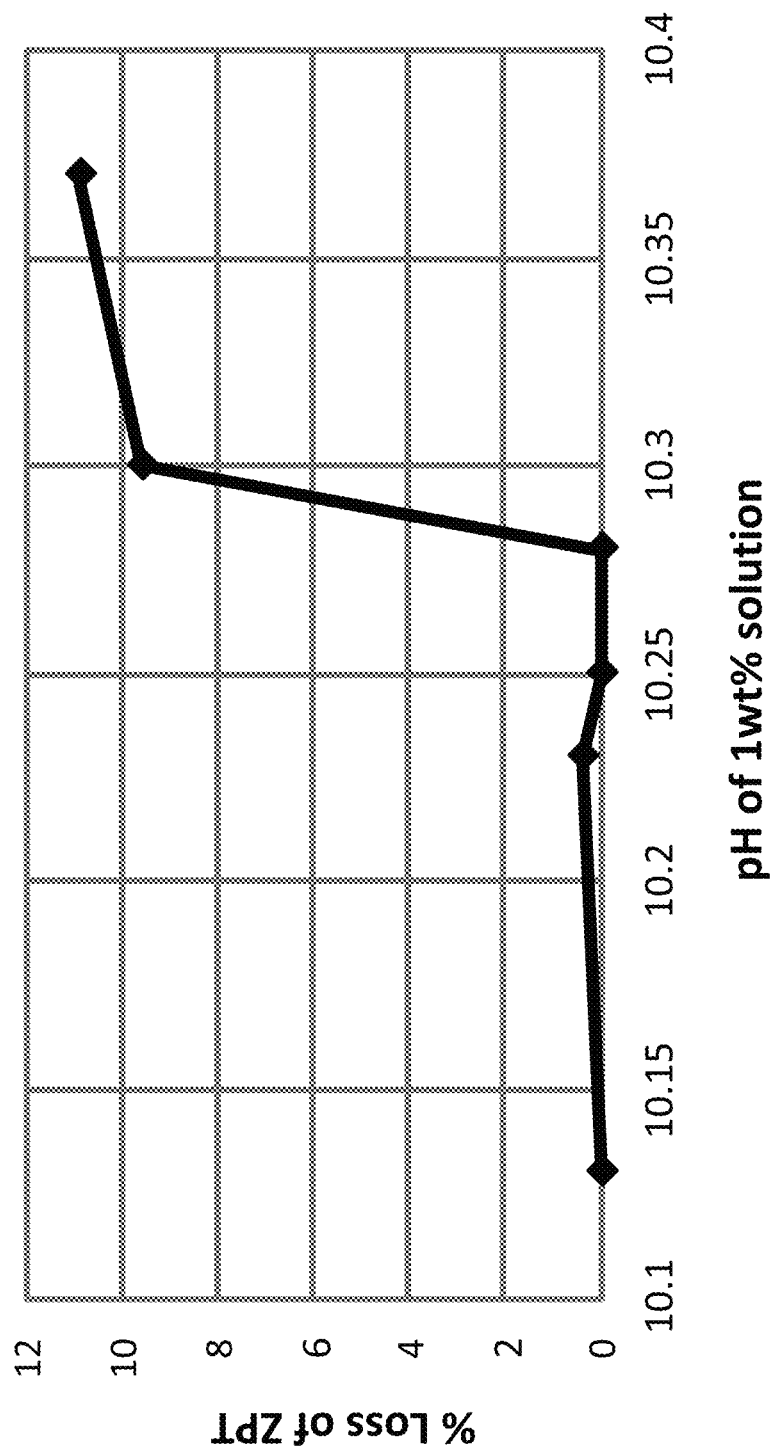
FIG. 1 is a graph showing the percentage loss of ZPT in four (4) exemplary bar soap compositions of the present invention and two (2) comparative bar soap compositions plotted as a function of the pH values of such bar soap compositions. The exemplary and comparative bar soap compositions were compositionally similar except for different pH values.

Except as otherwise noted, the articles "a", "an", and "the" mean "one or more." The term "comprising" means that other steps and other ingredients which do not affect the end result can be added, and this term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein. Particularly, the compositions of the present invention contain zinc pyrithione, at least one acidic pH adjusting agent, and at least one soap surfactant as the essential ingredients, and they may contain one or more additional or optional ingredients as described hereinafter.

All percentages, parts and ratios are based upon the total weight of the personal care compositions of the present invention, unless otherwise specified. All such weights as they pertain to listed ingredients are based on the active level and, therefore do not include carriers or by-products that may be included in commercially available materials.

The components, including those which may optionally be added, of the topical anti-microbial compositions of the present invention, as well as methods for preparation, and methods for use, are described in detail below.

All ratios are weight ratios unless specifically stated otherwise. All temperatures are in Celsius degrees, unless specifically stated otherwise. All dimensions and values disclosed herein (e.g., quantities, percentages, portions, and proportions) are not to be understood as being strictly limited to the exact numerical values recited. Instead, unless otherwise specified, each such dimension or value is intended to mean both the recited value and a functionally equivalent range surrounding that value. For example, a dimension disclosed as "40 mm" is intended to mean "about 40 mm."

Herein, the term "effective" means an amount of a subject active high enough to provide a significant positive modification of the condition to be treated. An effective amount of the subject active will vary with the particular condition being treated, the severity of the condition, the duration of the treatment, the nature of concurrent treatment, and like factors.

Zinc Pyrithione

Zinc pyrithione is incorporated in the bar soap compositions of the present invention in the form of a combination, a mixture, a dispersion, a suspension, or an emulsion. Preferably, but not necessarily, zinc pyrithione is present in a spherical or platelet form, while the zinc pyrithione particles have an average size of up to about 20 μm, more preferably up to about 5 μm, and most preferably up to about 2.5 μm. Alternatively, zinc pyrithione is present in a particulate form that is non-platelet and non-spherical, having a configuration selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof, as described by U.S. Pat. No. 6,242,007.

Zinc pyrithione (or ZPT) used in the present invention may be made by reacting 1-hydroxy-2-pyridinethione (i.e., pyrithione acid) or a soluble salt thereof with a zinc salt (e.g., $ZnSO_4$) to form a zinc pyrithione precipitate, as illustrated by the disclosures of U.S. Pat. No. 2,809,971, or by any other methods currently known in the art. It is commercially available as an aqueous dispersion containing 48% active ZPT from Arch Chemical.

While higher concentrations of zinc pyrithione have been observed to control the growth of a wider range of microorganisms, the useful amount of zinc pyrithione that can be added to a commercial product is limited by efficacy and economic considerations, and environmental concerns. In personal care compositions, such as soaps, the amount of zinc pyrithione that may be added is further limited by toxicological concerns. Preferably, but not necessarily, the bar soap compositions of the present invention contains zinc pyrithione in the amount ranging from about 0.01% to about 5% by total weight of such compositions. More preferably, such compositions contains from about 0.1% to about 2.0% by weight of zinc pyrithione.

Stabilization of Zinc Pyrithione

Inventors of the present invention have discovered that stability of zinc pyrithione in a soap composition is highly dependent on the pH value of such a composition Zinc pyrithione remains relatively stable in soap compositions with pH values below 9.6. However, there is surprisingly and unexpectedly a critical pH window ranging from about 9.6 to about 10.3, which is crucial for the maintenance of zinc pyrithione stability in bar soap compositions, and beyond which even a slight pH increase may lead to significant loss of zinc pyrithione and thereby render the soap compositions ineffective for anti-microbial purposes.

Conventional art in the soap-making industry has not recognized or appreciated the high sensitivity of zinc pyrithione towards the pH value within this critical pH window in soap compositions. Because relatively high pH values (i.e., above 10) are desirable in soap compositions in light of the needs for full saponification of the fatty acids during the soap-making processes and for effectively controlling microorganism growth so as to provide a satisfactory cleansing effect, most bar soaps currently on the market are formed with pH values above this critical pH window.

As shown in the comparative examples hereinafter, inventors of the present invention have tested various commercially available bar soaps claiming a zinc pyrithione content of 2%, and found that the actual amount of zinc pyrithione detected in such bar soaps is far less than the amount claimed, indicating that most or at least a substantial portion of zinc pyrithione in these bar soap compositions has undergone oxidation and is therefore no longer detectable. Because the loss of zinc pyrithione occurs gradually over an extended period of time, it is not detectable by the normal quality control process, which is typically conducted immediately after the manufacturing process. Correspondingly, the zinc pyrithione instability problem was never noticed, let alone addressed, by the manufacturers of these commercially available soaps.

Inventors of the present invention discovered that the high pH values of these commercially available bar soaps (e.g., from 10.4 to 10.7) are contributing to the zinc pyrithione instability in these commercial bar soaps, that there is a critical pH window for stabilization of zinc pyrithione in soaps, and that by precise modulation of the pH value with this critical pH window, zinc pyrithione can be effectively incorporated into and stabilized in a bar soap composition with little or no risk of loss. Specifically, inventors of the present invention discovered that when the pH value of the bar soap formulation is limited to the particular range that is higher than about 9.6 and lower than about 10.3 (measured at a 1 wt % solution), preferably from about 9.80 to about 10.25, and more preferably from about 10.0 to about 10.2, zinc pyrithione can remain stable in the bar soap formulation, i.e., with little or no loss after extended periods of time. Consequently, the present invention enables the formation of improved bar soaps that contain stabilized zinc pyrithione, which are characterized by longer shelf stability and sustained anti-microbial effect, in comparison with the ZPT-containing soaps that are currently available on the market.

FIG. 1 is a graph that plots the percentage losses of ZPT over the pH values measured for bar soap compositions that were compositionally similar but had different pH values ranging from about 10.13 to about 10.37. Significantly different percentage losses of ZPT were observed for these bar soap compositions. Specifically, little or no percentage losses of ZPT were observed in bar soap compositions with pH less than about 10.3, but once the pH reaches 10.3 and above, the percentage losses of ZPT suddenly increase to more than 5%, which is detrimental for a ZPT-based commercial soap product.

The pH value of a bar soap composition is measured in aqueous solution at about 25° C., and it can be measured using any commercially available pH meter calibrated with pH standard solutions, such as, for example, the Seven-Multi™ pH meter available from Mettler Toledo International, Inc. (Switzerland). Specifically, a bar soap composition whose pH value is to be measured is first dissolved in distilled water at a concentration of 1 wt % and a temperature of 35° C. by agitation provided by a magnetic stir bar in a sealed container for one hour. The soap solution is then cooled to about 25° C. (+/−0.2° C.), and the pH is measured. The pH of the 1 wt % aqueous solution is then recorded as the pH of the bar soap composition.

PH Modulation

The present invention may achieve the above-described precise modulation of pH value of the bar soap composition by various mechanism.

In one specific embodiment of the present invention, the pH modulation is achieved through employment of an acidic pH adjusting agent. Any acid suitable for use in bar soap formulation, e.g., either an inorganic acid or an organic acid, can be employed in the practice of the present invention.

Examples of inorganic acid suitable for practice of the present invention include, but are not limited to: hydrochloric acid, sulfuric acid, sulphurous acid, nitric acid, nitrous acid, phosphoric acid, boric acid, and the like. Among these inorganic acids, sulfuric acid, nitric acid, and hydrochloric acid are preferred.

Suitable organic acids include carboxylic acids, sulfonic acids and fatty acids. Examples of carboxylic acids suitable for practice of the present invention include, but are not limited to: lactic acid, acetic acid, glycolic acid, malic acid, fumaric acid, citric acid, tartaric acid, oxalic acid, formic acid, benzoic acid, ascorbic acid, propionic acid, butyric acid, valeric acid, and the like. Examples of sulfonic acids include, but are not limited to: methanesulfonic acid, toluenesulfonic acid, taurine, and the like. Examples of other types of organic acids include, but are not limited to: aconitic acid (1,2,3-propene tricarboxylic acid), alginic acid, amino acids, azelaic acid, betulinic acid, boswellia acid (frankincense extract), cinnamic acid, dehydroacetic acid, hyaluronic acid, lipoic acid, pantothenic acid, phthalic acid, sorbic acid, sugar acid, thioglycolic acid, tranexamic acid, trichloroacetic acid, undecylenic acid, vitamin A acid, and the like. Preferred organic acids for the practice of the present invention include citric acid, lactic acid, acetic acid, fumaric acid, tartaric acid, oxalic acid, formic acid, malic acid, phosphoric acid, benzoic acid, and ascorbic acid. These organic acids can be easily incorporated into soap compositions either as liquids or solids.

Fatty acids are particularly preferred acidic pH adjusting agents for the practice of the present invention. When incorporated into the bar soap compositions of the present invention, the fatty acids can not only modulate the pH values of such compositions, but also contribute to the texture, lather properties and other aesthetics thereof. Any fatty acids with total carbon numbers ranging from $C_6$ to $C_{24}$ can be used for the practice of the present invention. The fatty acids can be either naturally derived or synthesized. They can be saturated or unsaturated, linear or branched. In a preferred embodiment of the present invention, the fatty acids used are derived from a natural source, such as plants (e.g., coconut, soy, cotton seed, olive, sunflower seed, palm, palm kernel, and the like) or animals (e.g., tallow, emu oil, butter, fish oil, and the like). Fatty acids with shorter carbon chains (e.g., $C_6$ to $C_{11}$, either linear or branched) are preferred when it is desirable to quickly integrate the fatty acids into an existing soap structure without heating.

Exemplary fatty acids include, but are not limited to: caproic acid, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and the like. Particularly useful fatty acids for the practice of the present invention are saturated or unsaturated fatty acids with total carbon numbers ranging from $C_{12}$ to $C_{22}$, such as, for example, lauric acid, myristic acid, palmitic acid, stearic acid, palmitoleic acid, oleic acid, and behenic acid.

The amount of acidic pH adjusting agent to be used in the bar soap compositions of the present invention depends on the acidity of such agent. For stronger acids, a lesser amount is required, while for weaker acids, a larger amount is needed. Therefore, the amount of acidic pH adjusting agent contained in the bar soap compositions of the present invention may vary widely from about 0.01% to about 10% by total weight of the compositions. When the acidic pH adjusting agent is a saturated or unsaturated free fatty acid, the amount to be employed may range from about 0.05% to about 5%.

In an alternative embodiment of the present invention, the pH modulation can be achieved by adjusting the amounts of raw materials used for soap-making, i.e., fats, oils, and base materials such as sodium or potassium hydroxide, so as to reach a final bar soap composition with the desired pH value. In yet another alternative embodiment of the present invention, the pH modulation can be achieved using a pH buffering agent, such as potassium carbonate or zinc carbonate.

Percentage Loss of Zinc Pyrithione

In a specific embodiment of the present invention, chemical stability of zinc pyrithione is evaluated by an aging test described as follows, so as to determine the percentage loss of zinc pyrithione after such aging test.

First, a bar soap containing zinc pyrithione is obtained, preferably immediately after it is manufactured. The starting content of zinc pyrithione in such bar soap (in percentage) is measured by method described hereinafter using a portion of the bar soap, or a companion bar made from the same batch of soap noodle. The bar soap is weighed (+/−0.01 g), and its starting weight is recorded. Second, the bar soap is subjected to an aging process, during which the bar soap is placed inside a sealed water impermeable bag, which is preferably made of polyethylene (PE). The bag containing the bar soap is then left either at room temperature (i.e., about 25° C.), or in a convection oven at an elevated temperature (e.g., 50° C.), for an extended period (e.g., 10 days, 12 days, 14 days, or up to 35 months in certain cases). After the aging, if placed in a convection over at the elevated temperature, the bar soap is taken out of the convection oven and allowed to return to room temperature (i.e., 25° C.). The bar soap is weighed again, and its final weight is recorded. The final content of zinc pyrithione in the bar soap (in percentage) is measured by the same method as described hereinafter.

Chemical stability of the zinc pyrithione is calculated by the following equation to obtain the percentage loss of zinc pyrithione:

$$\% \text{ Loss of } ZPT = \left[1 - \frac{\text{Final Weight} \times \text{Final } ZPT \text{ Content (\%)}}{\text{Starting Weight} \times \text{Starting } ZPT \text{ Content (\%)}}\right] \times 100$$

Preferably, the percentage loss of zinc pyrithione in the bar soap composition of the present invention is no greater than 10% after the bar soap composition is placed at an elevated temperature of 50° C. for 12 days. More preferably, the percentage loss of zinc pyrithione is no greater than 5%, and most preferably, the percentage loss is no greater than 2%, after the bar soap composition is subjected to an elevated temperature of 50° C. for 12 days.

Measurement of ZPT Content in Bar Soap Compositions

The content of zinc pyrithione in bar soap compositions is measured herein by an iodine-based titration method, which is described in greater detail in the following sections. The mercapto group in zinc pyrithione can be titrated by iodine, which oxidizes it to the disulfide-2,2' dithiobispyridine-1-oxide. If zinc pyrithione has already been oxidized or undergone transformation otherwise so that it no longer possesses the mercapto group, it will not be detectible by the iodine-based titration method described hereinafter.

First, a standardized 0.04N iodine solution is prepared. Specifically, anhydrous sodium thiosulphate (with a minimum purity of 99%) is oven-dried for 2 hours at 105° C. and then stored in a dessicator. 0.05 grams (+/−0.0001 g) of the anhydrous sodium thiosulfate is weighed and placed into the 100 ml polypropylene beaker of an autotitrator, and 50 ml of deionized water is added to form a standard solution. The autotitrator used herein is preferably a Mettler DL25 or Mettler DM140-SC titrator with platinum ring electrode, which is commercially available from Mettler Toledo Internantional, Inc. (Switzerland), or an equivalent thereof. The autitrator is set up to titrate the standard sodium thiosulfate solution with the iodine solution that is being standardized. Bubbles are eliminated from the burette of the autotitrator, and titration is commenced. Such procedure is repeated twice more, and the results are averaged to obtain a standardized 0.04N iodine solution. The % relative standard deviation (RSD) should be less than 1% of the average.

Next, standardized 0.01N and 0.006N iodine solutions are prepared. Specifically, standardized 0.01N iodine solution is prepared using 0.10 g (+/−0.0001 g) sodium thiosulphate dissolved in 100 mL deionized water, using 10.0 ml pipetted into the 100 ml autotitrator breaker with 50 mL additional deionized water followed by the titration procedure. Standardized 0.006N iodine solution is prepared using 3.0 ml of a 0.01M sodium thiosulphate solution and 40 ml of a solvent (containing 13% v/v hydrochloric acid in 6% v/v butanol), followed by addition of 40 ml of 1:1 hexane/isopropanol. The autotitration procedure is subsequently carried out. The iodine solutions are standardized daily.

The bar soap whose ZPT content is to be measured is then shredded using a grater and stirred to form a homogenous mixture. 4.00 grams of the shredded soap is weighed and put into a clean, dry beaker of an autotitrator. 75 ml of hot 6% v/v butanol (which was heated in a boiling-water bath) and 5 ml of concentrated HCl (provided at room temperature) are then added into the beaker. The mixture is agitated vigorously so as to fully dissolve all soluble components. The beaker is subsequently placed in the autotitrator, and bubbles are completely eliminated from the burette.

The titration is then initiated and analyzed while the mixture is still warm. The mixture is vigorously agitated during the titration procedure. For compositions with less than 0.2% of ZPT by weight, titration is carried out using the 0.006N iodine solution. For compositions with higher ZPT concentrations, the initial starting sample weight can be reduced. Titration can be done either manually or by using autotitration procedure by those with skill in the art.

The ZPT content in the bar soap is calculated as follows:

$$ZPT \text{ Content (\%)} = \frac{\text{Volume of Iodine Solution (ml)} \times N \times 15.88\%}{\text{Sample Weight (g)}}$$

wherein N is the normality of the standardized iodine solution, and wherein 15.88% is a constant that is derived from:

$$15.88\% = \frac{\text{Molecular Weight of } ZPT \times 100\%}{\text{Number of Pyrithione per Molecule} \times 1000 \text{ ml/Liter}}$$
$$= \frac{371.6 \times 100\%}{2 \times 1000 \text{ ml/Liter}}$$

The above-described procedure is repeated three times for each bar soap composition whose ZPT content is to be measured, and the results are averaged to obtain a final ZPT content in percentage (%) for the specific bar soap. All chemical reagents employed hereinabove are high-purity reagents obtained from VWR Scientific (Batavia, Ill., USA) or other scientific chemical suppliers.

Soap Surfactants

The bar soap composition of the present invention will typically comprise one or more soap surfactants in the total amount of from about 20% to about 95%, preferably from about 60% to about 90%, and more preferably still from about 70% to about 80%, by total weight of the composition.

The term "soap" is used herein in its popular sense, i.e., the alkali metal, ammonium, or alkanolamine salts of $C_8$-$C_{24}$ fatty acids. Preferably, the soaps used herein are the well known alkali metal salts of $C_{12}$-$C_{22}$ fatty acids. More preferably, the soaps are alkali metal salts of $C_{12}$-$C_{18}$ fatty acids, which include, but are not limited to: sodium, magnesium, potassium, calcium, mono-, di- and tri-ethanol ammonium salts of lauric acid, myristic acid, palmitic acid, stearic acid, myristoleic acid, palmitoleic acid, sapienic acid, oleic acid, elaidic acid, vaccenic acid, linoleic acid, linoelaidic acid, α-linolenic acid, and combinations thereof. Most preferably, sodium-based $C_{12}$-$C_{18}$ fatty acid soaps are used in the compositions of this invention, but from about 1% to about 25% of the soap may be ammonium-, potassium-, magnesium-, calcium-based $C_{12}$-$C_{18}$ fatty acid soaps, or a mixture thereof.

Preferred soaps of the present invention include those made from naturally-derived fatty acids, such as animal- or plant-derived glycerides, including but not limited to: tallow, grease, lard, whale oil, fish oil, coconut oil, palm oil, palm kernel oil, babassu oil, soybean oil, peanut oil, rapeseed oil, castor oil, rice bran oil, as well as derivatives and modifications thereof. Soaps made from coconut oil may provide the lower end of the broad molecular weight range. Those soaps having the fatty acid distribution of peanut or rapeseed oil, or their hydrogenated derivatives, may provide the upper end of the broad molecular weight range.

The term "tallow", as used herein, means fatty acid mixtures with approximately 2-4% myristic acid, 25-35% palmitic acid, 20-25% stearic acid, 1-3% palmitoleic acid, 35-45% oleic acid and 2-4% linoleic acid. Other sources with similar fatty acid distributions, such as the fatty acids derived from palm stearin oil and from various animal tallows and lard, are also included within the term tallow. The tallow can also be hardened (i.e., hydrogenated) to convert part or all of the unsaturated fatty acid moieties to saturated fatty acid moieties.

The term "coconut oil" as used herein, means glycerides or fatty derivatives therefrom with fatty acid mixtures which typically have an approximate carbon chain length distribution of about 5-10% $C_8$, 5-10% $C_{10}$, 45-55% $C_{12}$, 15-20% $C_{14}$, 5-10% $C_{16}$, 1-3% $C_{18}$, 5-10% oleic acid, and 1-3% linoleic acid (the first six fatty acids listed being saturated). Other sources having similar fatty acid distributions, such as palm kernel oil and babassu oil, are included with the term coconut oil.

Particularly useful in the present invention are the sodium and/or potassium soaps made from a mixture of tallow, palm stearine, palm oil, and palm kernel and/or coconut oil. More specifically, the amount of tallow present in such mixture ranges from about 20% to about 80%, more preferably from about 30% to about 60%, and most preferably from about 40% to about 50%; the amount of palm stearine ranges from 0% to about 60%, more preferably from about 10% to about 50%, and most preferably from about 30% to about 40%; the amount of palm oil ranges from about 0% to about 40%, and more preferably from about 10% to about 30%; and the amount of palm kernel oil and/or coconut oil ranges from about 0% to about 50%, more preferably from about 10% to about 40%, and most preferably from about 20% to about 30%.

Another preferred soap surfactant consists of tallow soap and coconut soap, and preferably has a ratio of tallow soap versus coconut soap ranging from about 0.1:1 to about 9:1, and more preferably from about 1:1 to about 4:1.

Alkali metal soaps as described hereinabove can be made by direct saponification of the fats and oils, or by the neutralization of the corresponding free fatty acids which are prepared in a separate manufacturing process. For example, natural fats and oils such as tallow or coconut oil or their equivalents can be directly saponified with an alkali metal hydroxide using procedures well known to those skilled in the art. Alternatively, the soaps may be made by neutralizing free fatty acids, such as lauric acid ($C_{12}$), myristic acid ($C_{14}$), palmitic acid ($C_{16}$), stearic acid ($C_{18}$), or a mixture thereof with an alkali metal hydroxide or carbonate.

In one embodiment, the bar soap compositions of the present invention comprise soap made by a continuous soap manufacturing process. The soap, which comprises approximately 30% water, is then processed into soap noodles via a vacuum flash drying process. The soap noodles preferably comprise from about 70% to about 85% anhydrous soap and at least about 15% water. These percentage amounts are by total weight of the soap noodles. The soap noodles are then utilized in a milling process to make the finished bar soap compositions as described below.

Synthetic Surfactants

The bar soaps of the present invention may also contain one or more synthetic surfactants, in addition to the soap surfactants described hereinabove. Such synthetic surfactants can be selected from the group consisting of anionic surfactants, zwitterionic surfactants, amphoteric surfactants, cationic surfactants, nonionic surfactants, and a mixture or combination thereof.

Examples of anionic surfactants suitable for the practice of the present invention include, but are not limited to: alkyl sulfates, anionic acyl sarcosinates, acyl isethionates, alkyl ether sulfates, alkyl sulfosuccinates, trideceth sulfates, mixtures of ethoxylated alkyl sulfates and the like. Alkyl chains for these surfactants are preferably C10-18 and, more preferably, C12-14 alkyls.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, for example, carboxy, sulfonate, sulfate, phosphate, or phosphonate. Examples include alkyl betaines, alkyl amidoalkylbetaines and sulfobetaines, especially lauryl betaine, lauryl amidopropylbetaine, and cocoamidopropylbetaine.

Examples of amphoteric surfactants which can be used in the compositions of the present invention are those which can be broadly described as derivatives of aliphatic secondary and tertiary amines, in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition include the products sold under the trade name "Miranol" and described in U.S. Pat. No. 2,528,378.

Nonionic surfactants useful in this invention can be broadly defined as compounds produced by the condensation of alkylene oxide groups (hydrophilic in nature) with an organic hydrophobic compound, which may be aliphatic or alkyl aromatic in nature.

If synthetic surfactants are included in the bar soap compositions of the present invention, mild ones are preferred. A mild synthetic surfactant is defined herein as one which does relatively little damage to the barrier function of the stratum corneum layer of the skin. Standard tests are well known for determining the relative mildness of surfactants. Some preferred mild synthetic surfactants useful in the subject invention compositions include alkyl glyceryl ether sulfonates (AGS), anionic acyl sarcosinates, methyl acyl taurates, N-acyl glutamates, alkyl glucosides, acyl isethionates, alkyl sulfosuccinates, alkyl phosphate esters, ethoxylated alkyl phosphate esters, ethoxylated alkyl alcohols, alkyl sulfates, alkyl ether sulfates, methyl glucose esters, protein condensates, mixtures of alkyl ether sulfates and alkyl amine oxides, betaines, sultaines, and mixtures thereof. Included in the synthetic surfactants are the alkyl ether sulfates with from about 1 to about 12 ethoxy groups, especially ammonium and sodium lauryl ether sulfates.

Synthetic surfactants are present in the subject compositions at a level of from 0% to about 20%, preferably from 0% to about 10%.

Inorganic Salts

Inorganic salts can also be utilized in the present bar soap compositions to help maintain the water content of the present compositions. The inorganic salts help to bind water in the bar soap composition, thereby preventing water loss by evaporation. The present bar soap compositions comprise from about 0% to about 15%, of inorganic salts. Suitable inorganic salts include, but are not limited to: zinc sulfate, ammonium chloride, ammonium sulfate, calcium sulfate, ferric sulfate, magnesium chloride, magnesium sulfate, and the like. Magnesium salts, when used as an ingredient in the present bar soap compositions, tend to be converted to magnesium soap in the finished product. Sodium tripolyphosphate is useful as it can promote the generation of lather as the bar soap composition is used by a consumer for cleansing skin.

Carbohydrate Structurants

Carbohyrate structurants can optionally, but preferably, be included as ingredients in the present bar soap compositions. Suitable carbohydrate structurants as ingredients in the present compositions include, but are not limited to: raw starch (corn, rice, potato, wheat, and the like), pregelatinzed starch, carboxymethyl cellulose, stabylene, carbopol, carregeenan, xanthan gum, polyethylene glycol, polyethylene oxide, and the like. Preferred carbohydrate structurants include raw starch and/or pregelatinized starch.

A preferred carbohydrate structurant for incorporating in a bar soap composition is starch. The starch can be either raw starch or it can be pregelatinized starch. Alternatively, raw starch can be used and modified during the process of making the bar soap composition such that the starch becomes gelatinized, either partially or fully gelatinized. Pregelatinized starch is starch that has been gelatinized before added as an ingredient in the present bar soap compositions. Gelatinized starch, either partially or fully gelatinized starch, can be preferred for providing enhanced skin feel benefits, such as providing a soft and smooth skin feel. A preferred pregelatinized starch for use as an ingredient in the present compositions is PREGEL-A M 0300 commercially available from Tianjin Tingfung Starch Development Co., Ltd. of Tianjin, China.

The level of carbohydrate structurant in the present compositions is typically from about 1% to about 20%, preferably from about 2% to about 17%, and more preferably from about 4% to about 15%, by weight of the composition.

Humectants

The bar soap compositions of the present invention can further comprise a humectant. The humectants as used herein are generally selected from the group consisting of polyhydric alcohols, water soluble alkoxylated nonionic polymers, and mixtures thereof. The humectants herein are preferably used at levels ranging from about 0.1% to about 20%, more preferably from about 0.5% to about 15%, and most preferably from about 1% to about 10% by total weight of the composition.

Humectants, such as glycerin, can result from the production of anhydrous soap of the present invention by removing less glycerin as by product after saponification. The humectant can thus be a component of the soap noodle used in preparation of the present compositions. As a product of the anhydrous soap reaction, the level of humectant in the soap noodle is typically no more than about 1%, by weight of the soap noodle.

Incorporating additional humectants into the present bar soap compositions can result in a number of benefits such as improvement in hardness, decreased Water Activity, and lower weight loss rate of the bar soap composition over time, which were caused by water evaporation.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

Cationic Polymers

The present bar soap compositions can optionally further comprise cationic polymers to improve the lathering and skin feel benefits of the compositions. When present, the amount of cationic polymer in the bar soap composition will range from about 0.001% to about 10%, preferably from about 0.01% to about 5%, more preferably from about 0.05% to about 1%, by total weight of the composition. Preferred embodiments contain levels of cationic polymer of less than about 0.2%, preferably less than about 0.1%, by total weight of the composition. If the level of cationic polymer is too high, the resulting bar soap composition can exhibit a sticky skin feel.

Suitable cationic polymers for use in the present bar soap compositions include, but are not limited to: cationic polysaccharides; cationic copolymers of saccharides and synthetic cationic monomers; cationic polyalkylene imines; cationic ethoxy polyalkylene imines; cationic poly[N-[3-(dimethylammonio)propyl]-N'[3-(ethyleneoxyethylene dimethyl ammonio) propyl]urea dichloride]. Suitable cationic polymers generally include polymers having a quaternary ammonium or substituted ammonium ion.

Non-limiting examples of suitable cationic polymers for use herein include cationic hydroxyethyl cellulose (available under the tradename Ucare Polymer JR400®, Ucare Polymer JR-125®. or Ucare Polymer LR-400® from Amerchol); cationic starches (available under the tradename STALOK® 100, 200, 300, and 400 from Staley, Inc.); cationic galactomannans based on guar gum (available under the tradename Galactasol® 800 series from Henkel, Inc. and under the tradename JAGUAR® from Meyhall Chemicals, Ltd.). A preferred cationic polymer is guar hydroxypropyl trimonium chloride available from Meyhall Chemicals, Ltd. under the tradename JAGUAR® C13S.

Brighteners

Brighteners can be included as optional ingredients in the bar soap composition of the present invention at a level of from about 0.001% to about 1%, preferably from about 0.005% to about 0.5%, and more preferably from about 0.01% to about 0.1%, by total weight of the composition. Examples of suitable brighteners in the compositions of the present invention include disodium 4,4'-bis-(2-sulfostyril)-biphenyl (commercially available under the tradename Brightener-49, from Ciba Specialty Chemicals); disodium-4,4'-bis-[(4,6-di-anilino-s-triazine-2-yl)-amino]-2,2'-stilbenedi-sulfonate (commercially available under the tradename Brightener 36, from Ciba Specialty Chemicals); 4,4'-bis-[(4-anilino-6-morpholino-s-triazine-2-yl)-amino]-2,2'-stilbenedi-sulfonate (commercially available under the tradename Brightener 15, from Ciba Specialty Chemicals); and 4,4'-bis-[(4-anilino-6-bis-2(2-hydroxy-yethyl)-amino-s- triazine-2-yl)-amin-o]-2,2'-stilbenedisulfonate (commercially available under the tradename Brightener 3, from Ciba Specialty Chemicals); and mixtures thereof.

Silica

Silica, or silicon dioxide, can be optionally incorporated in the present bar soap compositions at a level of from about 0.1% to about 15%, preferably from about 1% to about 10%, and more preferably from about 3% to about 7%, by total weight of the composition. Silica is available in a variety of different forms include crystalline, amorphous, fumed, precipitated, gel, and colloidal. Preferred forms herein are fumed and/or precipitated silica.

Thickening silica typically has smaller particle size versus normal abrasive silica and is preferred herein. The average particle size of thickening silica is preferably from about 9 μm to about 13 μm, as opposed to normal abrasive silica which has an average particle size of from about 20 μm to about 50 μm. Due to the surface of the preferred thickening silica having a relatively large amount of silinol groups, it can bind water and build the right texture for the present bar soap compositions. The silinol groups tend to form hydrobond with water, wherein three-dimensional networks are formed thereby to act like a spring in the soap phase to deliver good foaming and good texture. The thickening silica preferably has a high oil absorbency value (DBP), normally indicating porosity and large surface area, and is preferably greater than about 250 (g/100 g), and more preferably greater than about 300 (g/100 g).

Non-limiting examples of suitable thickening silica include: SIDENT 22S commercially available from Degussa; ZEODENT 165 commercially available from J. M. Huber Corp.; SORBOSIL TC15 commercially available from Ineos Silicas; TIXOSIL 43 commercially available from Rhodia.

Other optional ingredients in the present bar soap compositions include, but are not limited to: perfumes; and coloring agents, opacifiers and pearlizers such as titanium dioxide; all of which are useful in enhancing the appearance or cosmetic properties of the product.

Water Activity

Water Activity ("Aw") is a measurement of the energy status of the water in a system. It indicates how tightly water is bound, structurally or chemically, within a composition. Water activity ("Aw") is defined as the ratio of the water vapor pressure over a sample (P) to that over pure water ($P_0$):

$$A_W = \frac{P}{P_0}$$

Water activity of a sample composition can be measured electronically using a water activity meter with a sealed chamber and an electrical or optical measurement of the headspace. The meter is calibrated against a series of saturated salt solutions. A sample composition to be measured is placed in the chamber held at ambient temperature which is then allowed to equilibrate with the headspace in the chamber. At equilibrium, the relative humidity of the air in the chamber is the same as the water activity of the sample.

For purposes of the present invention, the water activity (Aw) of a bar soap composition can be measured using a Hygrolab 3 Water Activity Meter available from Rotronic, Inc. (Huntington, N.Y., USA). The following procedure is employed to determine the water activity (Aw) of a bar soap composition:

1. Check the chamber of the meter to make sure it is clean and dry before the test;
2. Cut a bar soap into pieces of about 0.2-0.4 cm thick with a stainless steel knife;
3. Put the soap pieces into a clean, dry plastic sample container with a depth of ½";
4. Press the soap pieces with a gloved finger lightly to make sure that the bottom of the container is covered by the soap pieces;
5. Put the sample container back into the chamber of the meter and cover it with the chamber top, which contains the electronic headspace measurement apparatus;
6. Wait for the headspace to reach equilibrium (approximately 1-2 hours); and
7. Record the temperature and the Aw value.

Preferably, but not necessarily, the bar soap compositions of the present invention are characterized by a water activity of less than 0.9, more preferably between about 0.4 and 0.9, still more preferably between 0.5 and 0.9, and most preferably between 0.6 and 0.9. The bar soap can be manufactured with a water activity of about 0.85, and during distribution, such bar soap can dehydrate to obtain a lower water activity of between 0.5 and 0.8, or between 0.55 and 0.75, or between 0.6 and 0.75.

The cleansing bar soap compositions of the present invention can be used by consumers to cleanse skin during bathing or washing.

Process of Manufacture

The bar soap composition of the present invention can be made via a number of different processes known in the art. Preferably, the present compositions are made via a milling process, resulting in milled bar soap compositions.

A typical milling process of manufacturing a bar soap composition includes: (a) a crutching step in which the soap is made, (b) a vacuum drying step in which the soap is made into soap noodles, (c) an amalgamating step in which the soap noodles are combined with other ingredients of the bar soap composition, (d) a milling step in which a relatively homogeneous mixture is obtained, (e) a plodding step in which the soap mixture is extruded as soap logs and then cut into soap plugs, and (f) a stamping step in which the soap plugs are stamped to yield the finished bar soap composition.

EXAMPLES

Examples 1-9

Bar soap compositions as illustrated in Examples 1 through 9 hereinafter exemplify specific but non-limiting embodiments of the present invention. They were prepared using soap noodles that were made via a conventional process, involving a crutching step and a vacuum drying step. Soap noodles prepared from batch kettle processes are also suitable for practice of the present invention. Soap noodles used in the following specific examples had the following approximate proportions (%) of soap surfactants (by total weight of the soap noodles): from about 80% to about 90% anhydrous soap, which contained from about 40% to about 50% tallow (TLO), from about 30% to about 45% palm oil stearine (POS), and from about 15% to about 25% palm kernel oil (PKO) or coconut oil (CO).

Such soap noodles were added to an amalgamator and mixed with other ingredients. First, optional ingredients such as perfume, brightener, and titanium dioxide were added to the amalgamator and mixed for about 15 seconds. Water, inorganic salts (such as sodium tripolyphosphate, tetrasodium pyrophosphate, zinc carbonate and/or magnesium sulfate), fatty acids, carbohydrate structurant (such as starch), were then added to the amalgamator and mixed for about 30 to 45 seconds. Zinc pyrithione was then added as a solid powder material or as an aqueous dispersion. As a solid powder, it was generally added during the first mixing step, and as an aqueous dispersion, it was generally added during the second mixing step. This soap mixture was then processed through a conventional 3- or 4-roll mill twice, plodded or extruded twice, and then cut and stamped to yield the following bar soap compositions.

Bar soap compositions of Examples 1 through 9 hereinafter were prepared from the same soap noodles via the same soap-making process as described hereinabove, but with different pH values that were effectuated by using trace amount of hydrochloric acid and/or sodium hydroxide.

The bar soap compositions of Examples 1-9 were aged under different conditions, i.e., at different temperatures, in different containers, and for different time periods, as described in detail hereinafter. All compositions were stored in either sealed polyethylene (PE) bags or in cardboard soap cartons and left in darkness. After the aging process, the ZPT content (%) was measured and then compared to either the initial amount in the formula or to the analytically determined ZPT content in the bars immediately after the soap-making process, so as to determine the percentage loss of ZPT in these compositions, which are recorded at below:

TABLE 1

| | | Example 1 | Example 2 | Example 3 | Example 4 | Example 5 |
|---|---|---|---|---|---|---|
| | Soap Noodle | 97.68% | 96.54% | 98.30% | 97.30% | 98.58% |
| | TiO$_2$* | 0% | 0% | 0.49% | 0.4% | 0.4% |
| | Starch | 0% | 0% | 0% | 0% | 0% |
| | ZPT** | 0.50% | 0.25% | 0.20% | 0.50% | 0.50% |
| | ZnCO$_3$ | 0% | 1% | 0.79% | 0% | 0% |
| | Perfume | 0% | 0% | 0% | 1% | 0% |
| | Water | QS | QS | QS | QS | QS |
| | Aw | 0.77 | 0.69 | 0.80 | 0.50 | 0.62 |
| | pH*** | 10.12 | 10.18 | 10.25 | 10.05 | 10.20 |
| Storage condition 1 | | 25° C. for 2 months in PE bag | 25° C. for 14 days in PE bag | 25° C. for 14 days in PE bag | 25° C. for 32 days in PE bag | 50° C. for 10 days in cardboard carton |
| Results | ZPT Content | 0.49% | 0.25% | 0.20% | 0.49% | 0.485% |
| | % loss of ZPT | 2.0% | 0% | 0% | 2.0% | 3.0% |
| Storage condition 2 | | 25° C. for 35 months in PE bag | 25° C. for 13 months in PE bag | 25° C. for 4.7 months in PE bag | 25° C. for 5.9 months plus 50° C. for 10 days | |
| Results | ZPT Content | 0.48% | 0.25% | 0.20% | 0.49% | |
| | % loss of ZPT | 5.88% | 0% | 0% | 0% | |

| | | Example 6 | Example 7 | Example 8 | Example 9 |
|---|---|---|---|---|---|
| | Soap Noodle | 96.28% | 96.21% | 96.28% | 96.28% |
| | TiO$_2$* | 0% | 0% | 0% | 0% |
| | Starch | 0% | 0% | 0% | 0% |
| | ZPT** | 0.50% | 0.512% | 0.50% | 0.495% |
| | ZnCO$_3$ | 0% | 0% | 0% | 0% |
| | Perfume | 0.116% (hexyl cinnamic aldehyde) | 0.116% (hexyl cinnamic aldehyde) | 0.072% (anisic aldehyde) | 0.073% (orange terpenes) |
| | Water | QS | QS | QS | QS |
| | Aw | 0.871 | 0.883 | 0.875 | 0.878 |
| | pH*** | 10.13 | 10.23 | 10.28 | 10.25 |
| Storage condition 1 | | 50° C. for 10 days in cardboard carton | 50° C. for 10 days in cardboard carton | 50° C. for 10 days in cardboard carton | 50° C. for 10 days in cardboard carton |
| | ZPT Content | 0.52%**** | 0.510% | 0.505%**** | 0.495% |
| | % loss of ZPT | 0% | 0.4% | 0% | 0% |

*Anatase powder
**ZPT particles purchased from FPS Lonza Chemicals Fine with an average diameter of about 0.75 micron, as dispersed in an aqueous solution containing 48% active ZPT
***Measured in a 1 wt % aqueous solution.
****The observed increase in ZPT content after storage (in comparison with the original ZPT content) was due to the loss of water during the 10 days when the bar soap was stored in a cardboard carton. In this event, the percentage loss of ZPT was recorded as 0%, instead of a negative number.

Comparative Example 1

Five (5) different commercially available ZPT-containing bar soaps were purchased with the following claimed ingredients. These bar soaps were then analyzed for zinc pyrithione content according to the analytical method described hereinabove.

TABLE 2

|  | Comp. Example IA | Comp. Example IB | Comp. Example IIA | Comp. Example IIB | Comp. Example III |
|---|---|---|---|---|---|
| Product Name | DermaZinc ™ | DermaZinc ™ | Noble Formula ™ | Noble Formula ™ | Calming Zinc Bar |
| Manufacturer | Dermalogix Partners, Inc. (Scarborouh, ME, USA) | Dermalogix Partners, Inc. (Scarborouh, ME, USA) | Ontos, Inc. (Chehalis, WA, USA) | Ontos, Inc. (Chehalis, WA, USA) | Dr. Bailey Skin Care (Sebastopol, CA, USA) |
| Ingredients | Coconut oil, Deionized water, Sodium hydroxide, Olive oil, Vegetable oil, Glycerin, Wheat germ oil, Oatmeal | Coconut oil, Deionized water, Sodium hydroxide, Olive oil, Vegetable oil, Glycerin, Wheat germ oil, Oatmeal | Saponified olive oil (infused with *calendula*), Saponified emu oil, Ground oatmeal | Saponified olive oil (infused with *calendula*), Saponified emu oil, Ground oatmeal | Saponified olive oil (infused with *calendula*), Shea butter, Oatmeal |
| Labeled ZPT content | 2% | 2% | 2% | 2% | 2% |
| Water content | 3.75% | 10.29% | 3.02% | 9.96% | 5.63% |
| Aw | 0.47 | 0.62 | 0.48 | 0.59 | 0.53 |
| pH (in 1 wt % solution) | 10.74 | 10.51 | 10.34 | 10.43 | 10.44 |
| Measured ZPT content | 0.00% | 0.70% | 1.04% | 0.94% | 1.27% |
| Percentage Loss of ZPT* | 100% | 65% | 48% | 53% | 36.5% |

*The percentage loss of ZPT as provided herein was calculated based on the assumption that the starting ZPT content in these bar soaps was 2%, as claimed by the manufacturers on the product labels.

As shown in the comparative examples hereinabove, the actual ZPT contents in these commercially available bar soaps are far less than the 2% claimed by the manufacturers on the product labels. The likely explanation is that most, or at least a significant portion, of zinc pyrithione contained in these bar soaps were oxidized and are therefore no longer detectible by the iodine-based titration method described hereinabove. The pH values of these commercially available bar soaps are in the range of 10.4 to 10.7, which are above the pH range (i.e., from about 9.6 to 10.3, more preferably from about 9.8 to 10.25, and most preferable from about 10.0 to 10.2) as discovered by inventors of the present invention to be critical for zinc pyrithione stabilization. The high pH values in these commercially available bar soaps are believed to cause the observed percentage loss of zinc pyrithione.

Comparative Example 2

Comparative bar soap compositions A-G as listed hereinafter were prepared from the same soap noodles by the same soap-making process and then aged under the same aging conditions as described hereinabove for Examples 1-9, except that they have pH values high than Examples 1-9 as effectuated by addition of trace amount of sodium hydroxide and hydrochloric acid. The percentage losses of ZPT in the Comparative Examples A-G were recorded as follows:

TABLE 3

|  | Comp. Example A | Comp. Example B | Comp. Example C | Comp. Example D | Comp. Example E | Comp. Example F | Comp. Example G |
|---|---|---|---|---|---|---|---|
| Soap Noodle | 97.58% | 96.23% | 96.23% | 94% | 77% | 93% | 76% |
| TiO$_2$* | 0.4% | 0% | 0% | 0.4% | 0.4% | 0.4% | 0.4% |
| Starch | 0% | 0% | 0% | 0% | 17% | 0% | 17% |
| Brightener | 0% | 0% | 0% | 0.02% | 0.02% | 0.02% | 0.02% |
| ZPT** | 0.5% | 0.503% | 0.488% | 0.503% | 0.522% | 0.495% | 0.509% |
| Perfume | 1% | 0.072% (anisic aldehyde) | 0.073% (orange terpenes) | 0% | 0% | 1% | 1% |

TABLE 3-continued

|  |  | Comp. Example A | Comp. Example B | Comp. Example C | Comp. Example D | Comp. Example E | Comp. Example F | Comp. Example G |
|---|---|---|---|---|---|---|---|---|
|  | Water | QS | QS | QS | QS | QS | QS | QS |
|  | Aw | 0.864 | 0.879 | 0.868 | 0.871 | 0.866 | 0.845 | 0.858 |
|  | pH*** | 10.30 | 10.30 | 10.37 | 10.55 | 10.54 | 10.54 | 10.44 |
| Storage condition |  | 50° C. for 10 days in cardboard carton | 50° C. for 10 days in cardboard carton | 50° C. for 10 days in cardboard carton | 50° C. for 10 days in cardboard carton | 50° C. for 12 days in PE bag | 50° C. for 12 days in PE bag | 50° C. for 12 days in PE bag |
| Result | ZPT Content | 0.445 | 0.455 | 0.435 | 0.486% | 0.502% | 0.441% | 0.481% |
|  | % loss of ZPT | 11.0% | 9.6% | 10.9% | 3.4% | 3.9% | 11.0% | 5.4% |

*Anatase powder.
**ZPT particles purchased from FPS Lonza Chemicals Fine with an average diameter of about 0.75 micron, as dispersed in an aqueous solution containing 48% active ZPT.
***Measured in a 1 wt % aqueous solution.

FIG. 1 is a graph that plots the percentage losses of ZPT over the pH values of the bar soap compositions of the above-described Examples 6-9 and Comparative Examples B and C, which are compositionally similar except for their pH values. As clearly indicated by this graph, significantly different percentage losses of ZPT were observed in bar soap compositions that are otherwise similar but with different pH values. No or little percentage loss of ZPT was observed in bar soap compositions with pH less than 10.3 (as in Examples 6-9), but once the pH reaches 10.3 (as in Comparative Examples B and C), the percentage losses of ZPT suddenly increase to more than 5%. Note that the percentage losses of ZPT described here were observed after only 10 days at an elevated temperature of 50° C. More significant losses are expected for Comparative Examples B and C over a more extended period of time.

Further, the above-listed inventive Examples 1-9 with pH values within the critical pH range described herein have an average percentage loss of ZPT of 0.68%, in comparison with the average percentage losses of ZPT as high as 60.50% for the commercial Comparative Examples IA-III and 7.87% for Comparative Examples A-G, which are statistically significant differences.

Comparative Example 3

Comparative bar soap compositions I-V were prepared from the same soap noodles by the same soap-making process as described hereinabove for Examples 1-9, except that they have pH values higher than those of Examples 1-9. The higher pH values were effectuated by addition of zinc carbonate ($ZnCO_3$), which is a slow-dissolving, high pH buffering agents. The percentage losses of ZPT in the Comparative Examples I-V after being subjected to an aging process at 50° C. for 12 days in a polyethylene bag were then measured and recorded as follows:

TABLE 4

|  | $ZnCO_3$ (wt %) | pH* | % Loss of ZPT |
|---|---|---|---|
| I | 0.1% | 10.52 | 4.0% |
| II | 0.2% | 10.59 | 5.5% |
| III | 0.3% | 10.65 | 11.5% |
| IV | 0.4% | 10.76 | 23.0% |
| V | 0.5% | 10.85 | 28.0% |

Figure 2:
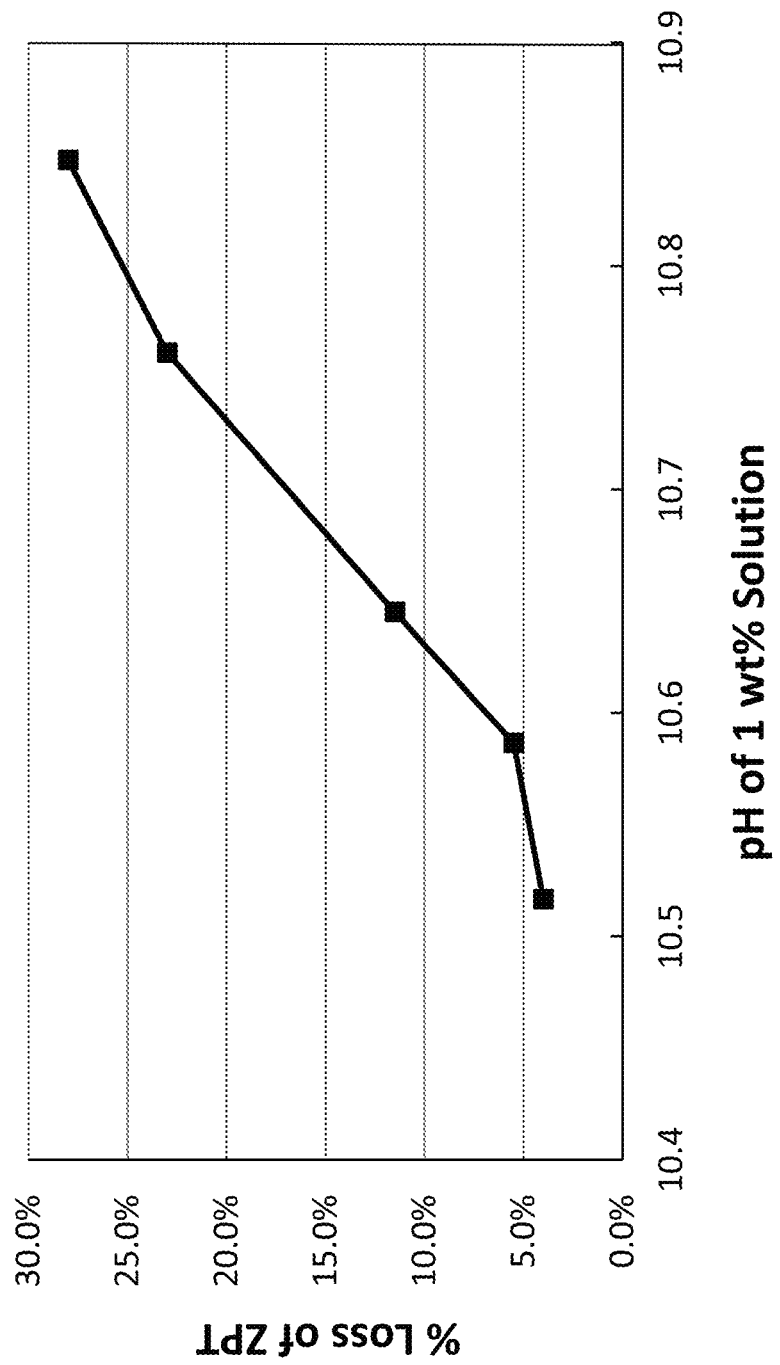
FIG. 2 is a graph showing the percentage loss of ZPT in five (5) comparative bar soap compositions plotted as a function of the pH values of such comparative bar soap compositions, which were compositionally similar except for different pH values as adjusted by a slow-dissolving pH buffering agent $ZnCO_3$.

FIG. 2 is a graph that plots the percentage losses of ZPT over the pH values of bar soap compositions of the above-described Comparative Examples I-V, which are compositionally similar except for their pH values as adjusted by the pH buffering agent $ZnCO_3$. It is clear from this graph that the percentage loss of ZPT increases with the pH value of the bar soap composition. The pH values of Comparative Examples I-V are all above the critical pH range of 9.6 to 10.3 as disclosed herein, and the percentage losses of ZPT in these bar soap compositions are higher than those observed in Examples 1-9 described hereinabove.

Comparative Example 4

Comparative bar soap compositions VI-XIII were prepared from the same soap noodles by the same soap-making process and then aged under the same aging conditions as described hereinabove for Examples 1-9, except that they have pH values higher than those of Examples 1-9. The higher pH values were effectuated by addition of potassium carbonate ($K_2CO_3$), which is a high pH buffering agent. The percentage losses of ZPT in Comparative Examples VI-XIII V after being subjected to an aging process at 50° C. for 12 days in a polyethylene bag were then measured and recorded as follows:

TABLE 5

|  | $K_2CO_3$ (wt %) | pH* | % Loss of ZPT |
|---|---|---|---|
| VI | 0.4% | 10.53 | 4.5% |
| VII | 0.8% | 10.56 | 8.0% |
| VIII | 1.0% | 10.57 | 11.0% |
| IX | 1.2% | 10.60 | 11.0% |
| X | 1.4% | 10.61 | 13.5% |
| XI | 1.6% | 10.62 | 15.0% |
| XII | 1.8% | 10.64 | 16.0% |
| XIII | 2.0% | 10.64 | 18.0% |

Figure 3:
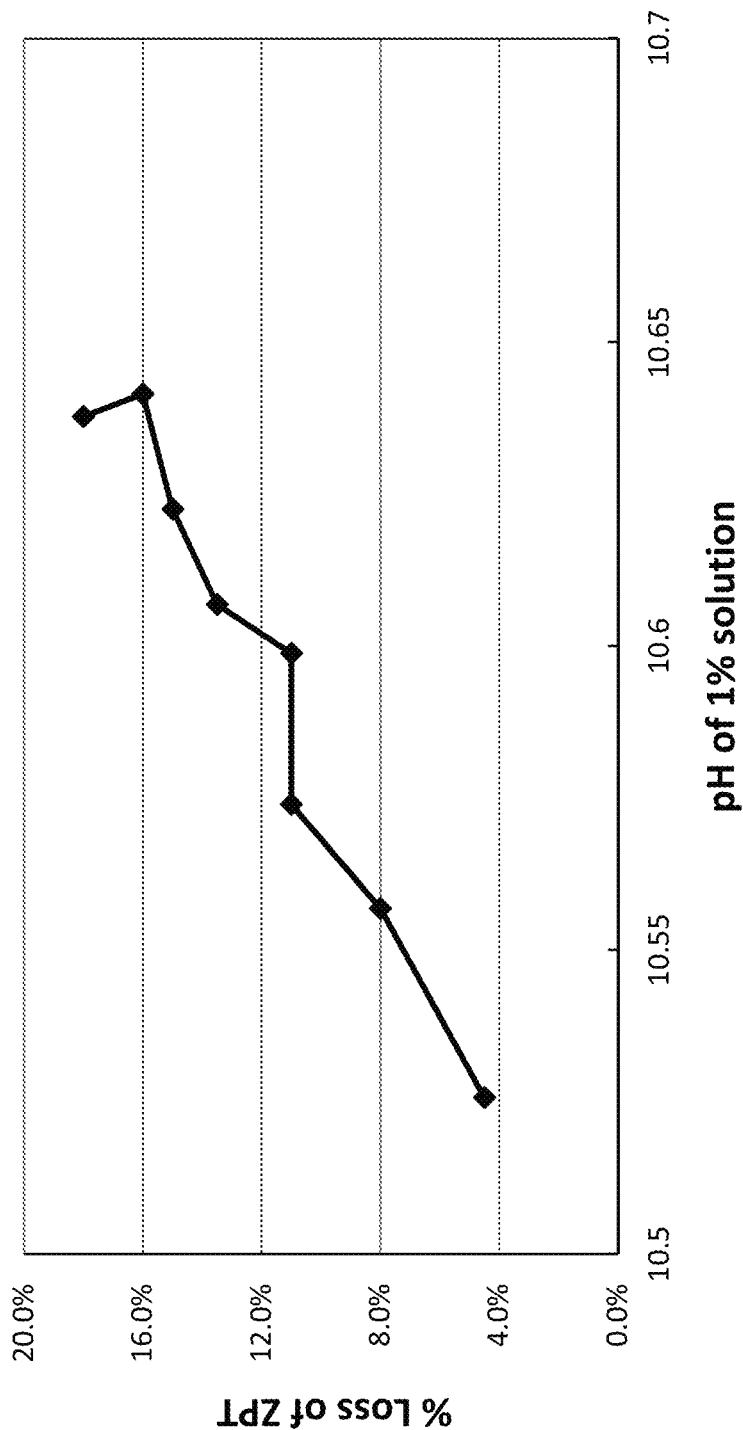
FIG. 3 is a graph showing the percentage loss of ZPT in eight (8) comparative bar soap compositions plotted as a function of the pH values of such comparative bar soap compositions, which were compositionally similar except for different pH values as adjusted by a pH buffering agent $K_2CO_3$.

FIG. 3 is a graph that plots the percentage losses of ZPT over the pH values of bar soap compositions of the above-described Comparative Examples VI-XIII, which are compositionally similar except for their pH values as adjusted by the pH buffering agent $K_2CO_3$. It is clear from this graph that the percentage loss of ZPT increases as the pH value of the bar soap composition increases. The pH values of Comparative Examples VI-XIII are above the critical pH range of 9.6 to 10.3 as disclosed herein, and the percentage losses of ZPT in these bar soap compositions are higher than those observed in Examples 1-9 described hereinabove.

Example 10

Following is an exemplary bar soap composition illustrative of a preferred, but not necessary, embodiment of the present invention.

| Ingredients | Amount (wt %) |
|---|---|
| Dry soap noodle* | 81.18 |
| Sodium palmate (from palm oil and palm oil sterine) | (49.683) |
| Sodium tallowate (from tallow) | (16.027) |
| Sodium palm kernelate (from palm kernel oil) | (14.424) |
| Unsaponifiable matter | (0.540) |
| Citric acid (anhydrous) | (0.100) |
| Sodium citrate | (0.152) |
| Pentasodium pentetate | (0.050) |
| Tetrasodum etidronate | (0.050) |
| Sodium chloride (low sodium) | (0.553) |
| Glycerine | (3.471) |
| Coconut acid | (0.950) |
| Water | (14.000) |
| Corn starch | 17.00 |
| Citric acid | 0.50 |
| Zinc pyrithione** | 0.42 |
| $TiO_2$ | 0.40 |
| Brightener slurry (4 wt % Brightener 49 and 96 wt % water) | 0.50 |
| Perfume (Pharolia) | 1.00 |

*The ingredients in italic are listed based on further compositional breakdowns of the dry soap noodle used herein, and the weight percentages of these ingredients as listed in the parenthesis add to a total of 100% for the dry soap noodle composition.
**ZPT particles purchased from FPS Lonza Chemicals Fine with an average diameter of about 0.75 micron, as dispersed in an aqueous solution containing 48% active ZPT.

Examples 11-15

The following bar soap compositions 11-15 can also be prepared from the same soap noodles by the same soap-making process as described hereinabove for Examples 1-9, except that different types of acids are added therein to modulate the pH values of these compositions, consistent with the principles and spirits of the present invention as described hereinabove.

| | Example 11 | Example 12 | Example 13 | Example 14 | Example 15 |
|---|---|---|---|---|---|
| Soap Noodle | 95.6% | 96.25% | 94% | 97.1% | 95.9% |
| $TiO_2$* | 0% | 0% | 0.49% | 0.4% | 0.4% |
| Lauric acid | 0% | 0% | 4% | 0% | 0% |
| Tartaric acid | 0% | 0% | 0% | 0.15% | 0% |
| Coconut fatty acids | 0% | 0% | 0% | 0% | 2% |
| Malic acid | 0% | 0.1% | 0% | 0% | 0.02% |
| Oleic acid | 1% | 0% | 0% | 0% | 0% |
| ZPT** | 0.20% | 0.25% | 0.20% | 0.50% | 0.50% |
| Perfume | 0% | 0% | 0% | 1% | 0% |
| Water | QS | QS | QS | QS | QS |

*Anatase powder.
**ZPT particles purchased from FPS Lonza Chemicals Fine with an average diameter of about 0.75 micron, as dispersed in an aqueous solution containing 48% active ZPT.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal cleansing composition comprising:
   (a) zinc pyrithione;
   (b) at least one soap surfactant; and
   (c) an acidic pH adjusting agent;
   wherein said personal cleansing composition is in the form of a bar soap, and wherein said personal cleansing composition is characterized by a pH value that is higher than about 9.6 and lower than about 10.3 when dispersed in an aqueous solution at 1 wt %.

2. The personal cleansing composition of claim 1, characterized by a pH value ranging from about 9.80 to about 10.25 when dispersed in a 1 wt % aqueous solution.

3. The personal cleansing composition of claim 1, characterized by a pH value ranging from about 10.0 to about 10.2 when dispersed in a 1 wt % aqueous solution.

4. The personal cleansing composition of claim 1, wherein the percentage loss of zinc pyrithione is no greater than about 10%, after said personal cleansing composition is placed at 50° C. for 12 days.

5. The personal cleansing composition of claim 1, wherein the percentage loss of zinc pyrithione is no greater than about 5%, after said personal cleansing composition is placed at 50° C. for 12 days.

6. The personal cleansing composition of claim 1, wherein the percentage loss of zinc pyrithione is no greater than about 2%, after said personal cleansing composition is placed at 50° C. for 12 days.

7. The personal cleansing composition of claim 1, wherein the at least one acidic pH adjusting agent is selected from the group consisting of inorganic acids, organic acids, and fatty acids.

8. The personal cleansing composition of claim 7, wherein said at least one acidic pH adjusting agent is an inorganic acid selected from the group consisting of hydrochloric acid, sulfuric acid, sulphurous acid, nitric acid, nitrous acid, phosphoric acid, boric acid, and combinations thereof.

9. The personal cleansing composition of claim 7, wherein said at least one acidic pH adjusting agent is an organic acid selected from the group consisting of lactic acid, acetic acid, glycolic acid, malic acid, fumaric acid, citric acid, tartaric acid, oxalic acid, formic acid, benzoic acid, ascorbic acid, propionic acid, butyric acid, valeric acid, methanesulfonic acid, toluenesulfonic acid, taurine, aconitic acid, alginic acid, amino acids, azelaic acid, betulinic acid, boswellia acid, cinnamic acid, dehydroacetic acid, hyaluronic acid, lipoic acid, pantothenic acid, phthalic acid, sorbic acid, sugar acid, thioglycolic acid, tranexamic acid, trichloroacetic acid, undecylenic acid, vitamin A acid, and combinations thereof.

10. The personal cleansing composition of claim 7, wherein said at least one acidic pH adjusting agent is a fatty acid selected from the group consisting of caproic acid, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and combinations thereof.

11. The personal cleansing composition of claim 1, wherein said at least one soap surfactant is selected from the group consisting of alkali metal, ammonium, and alkanolamine salts of $C_8$-$C_{24}$ fatty acids.

12. The personal cleansing composition of claim 1, characterized by a water activity of less than about 0.9.

13. A method for forming a bar soap, comprising the steps of:
(a) combining from about 0.01% to about 5% by weight of zinc pyrithione with from about 20% to about 95% by weight of at least one soap surfactant and an acidic pH adjusting agent; and
(b) shaping the mixture to form a bar soap,
wherein said bar soap is characterized by a pH value ranging that is higher than about 9.6 and lower than about 10.3 when dispersed in an aqueous solution at 1 wt %.

14. The method of claim 13, wherein the percentage loss of zinc pyrithione in the bar soap is no greater than about 5% after the bar soap is placed at 50° C. for 12 days.

15. The method of claim 13, wherein said at least one acidic pH adjusting agent is selected from the group consisting of sulfuric acid, nitric acid, hydrochloric acid, citric acid, lactic acid, acetic acid, fumaric acid, tartaric acid, oxalic acid, formic acid, malic acid, phosphoric acid, benzoic acid, ascorbic acid, lauric acid, myristic acid, palmitic acid, stearic acid, palmitoleic acid, oleic acid, behenic acid, and combinations thereof.

16. The method of claim 13, wherein said bar soap is characterized by a water activity of less than about 0.9.

* * * * *